US008028576B2

(12) United States Patent  
Oster

(10) Patent No.: US 8,028,576 B2  
(45) Date of Patent: Oct. 4, 2011

(54) MUSCLE STRENGTH ASSESSMENT SYSTEM

(76) Inventor: Jeffrey Arthur Oster, Granville, OH (US)

(*) Notice: Subject to any disclaimer, the term of this patent is extended or adjusted under 35 U.S.C. 154(b) by 57 days.

(21) Appl. No.: 12/396,275

(22) Filed: Mar. 2, 2009

(65) Prior Publication Data

US 2009/0227906 A1 Sep. 10, 2009

Related U.S. Application Data

(63) Continuation-in-part of application No. 11/457,959, filed on Jul. 17, 2006, now abandoned.

(60) Provisional application No. 60/699,839, filed on Jul. 15, 2005.

(51) Int. Cl.  
A61B 5/22 (2006.01)

(52) U.S. Cl. .................................. 73/379.01

(58) Field of Classification Search ............ 73/379.05; 600/587; 601/1; 482/148  
See application file for complete search history.

(56) References Cited

U.S. PATENT DOCUMENTS

| 4,858,621 | A | 8/1989 | Franks | |
|---|---|---|---|---|
| 6,228,000 | B1 * | 5/2001 | Jones | 482/8 |
| 6,672,157 | B2 * | 1/2004 | MacFarlane et al. | 73/379.01 |
| 6,706,003 | B2 * | 3/2004 | Perrad et al. | 600/587 |

OTHER PUBLICATIONS

Assal M, Shofer J B, Rohr E, Price R, Czerniecki J Assessment of an Electric Goniometer Designed to Measure Equinus Contracture. Journal of Rehabilitation Research and Development, 40: 235-240, 2003. 5 pages.

Van Gheluwe, B., Dananberg, Howard J.; Changes in Plantar Foot Pressure With In-Shoe Varus and Valgus Wedging; Journal of the American Podiatric Medical Association, vol. 94 No. I 1-11, 2004. 13 pages.

Veves A, Giurini J, LoGerfo F; The Diabetic Foot; Foot Pressure Abnormalities in the Diabetic Foot; Humana Press; 2nd Edition, 9:163-169. 7 pages.

Drerup B, Hafkemeyer U, Moller M, Wetz HH. Effect of gait velocity on pressure distribution in therapeutic footwear. Orthopade 30:169-75, 2001. English Abstract, Original in German. 7 pages.

Abbott BC, Bigland B, Ritchie JM, The Physiological Cost of Negative Work. J. Physiol. 117:380-390, 1952. 6 pages.

Ahroni JH, Boyko EJ, Forsberg R. Reliability of F-Scan in-shoe measurements of plantar pressure. Foot Ankle Int. 19:668-73, 1998. 7 pages.

Asmussen E Positive and Negative Muscular Work. Laboratory for theory of Gymnastics, University of Coenhagen, 1952. 22 pages.

Baldwin J, Cunningham K. Goniometry Under Attack: A Clinical Study Involving Physiotherapists. Physical Therapy Canada. 7974;26:74-7. 6 pages.

Barnett CH, A plastic pedograph. Lancet, 2:273, 1954. 2 pages.

Barnett S, Cunningham JL, West S. A comparison of vertical force and temporal parameters produced by an in-shoe pressure measuring system and a force platform. 5 pages.

Bauman JH, Brand PW. Measurement of Pressure Between Foot and Shoe. Lancet, 1:620, 1963. 5 pages.

(Continued)

Primary Examiner — Jewel V Thompson  
(74) Attorney, Agent, or Firm — Wood, Herron & Evans, LLP

(57) ABSTRACT

A system determines patient's muscle strength of a lever arm comprising a leg, ankle, and foot. A value indicative of the strength is determined based on pressure values associated with the lever arm, as well as at least one weight based value. The values may be entered remotely or locally to a computer that outputs the value indicative of the strength.

34 Claims, 5 Drawing Sheets

OTHER PUBLICATIONS

Betts RP, Duckworth TA. A Device for Measuring Plantar Pressures Under the Sole of the Foot. Engng in Med. 7:223-228, 1978. 6 pages.

Bigland B, Lippold OCJ. The relation between force, velocity and integrated electrical activity in human muscles. J Physiol 123:214-224, 1954. 11 pages.

Bobbert MF, Ingen Schenau GJ van. Coordination of Vertical Jumping. J. Biomechanics, 21, 241-262, 1988. 15 pages.

Carrier DR, Heglund NC, Earls KD. Variable gearing during locomotion in the human musculoskeletal system. Science 1994;265:651-3. 10 pages.

Close JR, Some applications of the functional anatomy of the ankle joint. J Bone Joint Surg 1956;38A:761-781. 22 pages.

Corrigan JP, Moore DP, Stephens MM. Effect of heel height on forefoot loading. Foot Ankle, 14:148-52, 1993. 6 pages.

Digiovanni CW, Holt S, Czerniecki JM, Ledous WR, Sangeorzan BJ. Can the Presence of Equinus Contracture Be Established by Physical Exam Alone? J Rehabil Res Dev 2001;38(3):335-40. 6 pages.

Elveru RA, Rothstein JM, Lamb RL. Goniometric Reliability in a Clinical Setting. Subtalar and Ankle Joint Measurements. Phys Ther 1988;68:672-7. 6 pages.

Falkel J. Plantar flexor strength testing using the Cybex isokinetic dynamometer. Phys Ther 58:847-850, 1978. 5 pages.

Ferris L, Sharkey NA, Smith TS, Mathews DK, Influence of Extrinsic Plantar Flexors on Forefoot Loading During Heel Rise; Foot and Ankle Int.16:464-473, 1995. 10 pages.

Fontenrose A, Miller J, and Hallum A. Physicians' and Physical Therapists' Evaluations of Cerebral-Palsied Children for Achilles Tendon Lengthening. Developmental Medicine of Child Neurology, 26:208-213, 1984. 6 pages.

Friederich JA, Brand RA, Muscle fiber architecture in the human lower limb. J Biomech. 23:91-95, 1990. 6 pages.

Gilliam TB, Sandy SP, Freedson PS, et al. Isokinetic torque levels for high school football players. Arch Phys Med Rehabil 60:110-114, 1979. 6 pages.

Godfrey CM, Lawson GA, Stewart WA. A Method for Determination of Pedal Pressure Changes During Weight Bearing: Preliminary Observations in Normal and Arthritic Feet. Arthritis and Rheumatism. 10:135-140. 1967. 7 pages.

Grundy M, Tosh PA McLeish RD Smidt L. An Investigation of the Centres of Pressure Under the Foot While Walking. J Bone Joint Surg. 57:98-103, 1975. 6 pages.

Hageman PA, Gillaspie DM, Hill LD. Effects of speed and limb dominance on eccentric and concentric isokinetic testing of the knee. J Orthop Sports Phys Ther 10: 59-65, 1988. 8 pages.

Hansen A, Childress D, Miff SC, Gard SA, Mesplay KP. The human ankle during walking: implications for design of biomimetic ankle protheses. J Biomechanics 2004;37:1467-1474. 8 pages.

Hart, DL, Stobbe TJ, Till CW, Plummer RW. Effect of trunk stabilization on quadriceps femoris muscle torque. Phys Ther 64:1375-1380, 1984. 6 pages.

Hawkins D, Bey M. Muscle and tendon force-length properties and their interactions in vivo. J Biomechanics 1997;30(1):63-70. 8 pages.

Hislop HJ, Perrine JJ, The isokinetic concept of exercise. Phys Ther 47:114-117, 1967. 5 pages.

Ho C-S, Lin C-J, Chou Y-L, Su F-C, Lin S-C. Foot progression angle and ankle joint complex in preschool children. Clin Biomechanics 2000:15:271-7. 7 pages.

Hof AL, Geelen BA, Van den Berg JW. Calf Muscle Moment, Work and Efficiency in Level Walking; Role of Series Elasticity. J Biomechanics 16:523-537, 1983. 17 pages.

Houtz SJ, Fischer FJ. Function of Leg Muscles Acting on Foot as Modified by Body Movements. J. Appl Physiol. 16 (4):597-605. 1961. 9 pages.

Hunter I, Kearney R. Dynamics of human ankle stiffness: variation with mean ankle torque. J Biomechanics 1982;15(10)147-752. 7 pages.

Ikai M, Steinhaus AH. Some Factors Modifying the Expression of Human Strength. J. Applied Physiology, 16:157-163, 1961. 7 pages.

Jacobs R, Bobbed MF, van Ingen Schenau GJ. Mechanical output from individual muscles during explosive leg extensions: the role of biarticular muscles. J Biomechanics 1996;29(4):513-523. 11 pages.

Jenkyn TR, Ehman RL, An K. Noninvasive muscle tension measurement using the novel technique of magnetic resonance elastography (MRE). J Biomechanics 2003;36:1917-1921. 5 pages.

Kadaba MP, Ramakrishnan HK, Wootten ME. Measurement of lower extremity kinematics during level walking. Journal of Orthopaedics Research 8:383-392, 1990. 11 pages.

Kannus P, Kaplan M. Angle-specific torques of thigh muscles: variability analysis in 200 healthy adults. Can J Sports Sci 16:264-270, 1991. 9 pages.

Kannus P, Yasuda K. Value of isokinetic angle-specific torque measurements in normal and injured knees. Med Sci Sports Exerc 24:292-297. 6 pages.

Kannus P. Isokinetic evaluation of muscular performance: Implications for muscle testing and rehabilitation. Int J Sports Med. 15:S11-S18, 1994. 8 pages.

Kepple TM, Siegel KL, Stanhope SJ. Relative contributions of the lower extremity joint moments to forward progression and support during gait. Gait and Posture 6:1-8, 1997. 8 pages.

Kernozek TW, LaMott EE, Dancisak MJ. Reliability of an in-shoe pressure measurement system during treadmill walking. Foot Ankle Int. 17:204-9, 1996. 7 pages.

Kim K, Uchiyama E, Kitaoka HB, An K. An in vitro study of individual ankle muscle actions on the center of pressure. Gait and Posture 2003;17:125-131. 7 pages.

Klein P, Mattys S, Rooze M. Moment arm length variations of selected muscles acting on talocrural and subtalar joints during movement: an in vitro study. J Biomechanics 1996;29(1):21-20. 10 pages.

Leardini A, Geometry and mechanics of the human ankle complex and ankle prosthesis design. Clinical Biomechanics 2001;16:706-709. 4 pages.

Leardini A, O'Connor JJ, Catani F, Giannini S. A geometric model of the human ankle joint. J Biomechanics 1999;32:585-591. 7 pages.

Leardini A, O'Connor JJ. A model for lever-arm length calculation of the flexor and extensor muscles at the ankle. Gait and Posture 2002;15:220-229. 11 pages.

Lord M, Hosein R, Williams RB. Method for in-shoe shear stress measurement. J. Biomed. Eng. 14:181-186, 1992. 6 pages.

Lundberg A, Svensson O, Nemeth G, Selvik G, The axis of rotation of the ankle joint. JBJS (Br) 1989;71-B:94-99. 6 pages.

Maurer BT, Siegler S, Hillstrom HJ, Selby-Silverstein L, Farrerr WD, Downey MS. Quantitative identification of ankle equinus with applications for treatment assessment. Gait and Posture 3:19-28, 1995. 10 pages.

McCully KK, Faulkner JA. Characteristics of lengthening contractions associated with injury to skeletal muscle fibers. J Appl Physiol 61:293-299. 1986. 9 pages.

Meinders M, Gitter A, Czerniecki JM. The role of ankle plantar flexor muscle work during walking. Scandinavian Journal of Rehabilitation medicine 30:39-46, 1998. 8 pages.

Miyahara, K. Pressure distribution on the sole in normal adult men during walking using the ANIMA-G2800 for recording. J. Jap. Orthop. Assoc. 67:449-462, 1993. Portions in English, Portions in Japanese. 14 pages.

Montgomery LC, Douglass LW, Deuster PA. Reliability of an isokinetic test of muscle strength and endurance. J Orthop Sports Phys Ther 11:315-322, 1989. 9 pages.

Murphy DF, Beynnon BD, Michelson JD, Vacek PM. Efficacy of plantar loading parameters during gait in terms of reliability, variability, effect of gender and relationship between contact area and plantar pressure. Foot Ankle Int. 26:171-9, 2005. 10 pages.

Neptune RR, Kautz SA, Zajac FE. Contributions of the individual ankle plantar flexors to support, forward progression and swing initiation during walking. J Biomechanics 2001;34:1387-1398. 12 pages.

Novacheck TF. The biomechanics of running. Gait and Posture 7:77-95, 1998. 19 pages.

Nyska M, McCabe C, Linge K, Laing P, Klenerman L. Effect of the shoe on plantar foot pressures. 66:53-6 Acta Orthop Scand. 5 pages.

O'Connell AL. Electromyographic Study of Certain Leg Muscles During Movements of the Free Foot and During Standing. 13 pages.

Orendurff MS, Aiona MD, Dorociak RD, Pierce RA. Length and force of the gastrocnemius and soleus during gait following tendo Achilles lengthenings in children with equinus. Gait and Posture 2002;15:130-135. 7 pages.

Pandya S, Florence JM, King WM, Robison JD, Oxman M, Province MA. Related Articles. Reliability of Goniometric Measurements in Patients With Duchenne Muscular Dystrophy. Phys Ther Sep. 1985;65: (9):1339-42. 4 pages.

Praet SF, Louwerens JW. The Influence of Shoe Design on plantar pressures in neuropathic feet. Diabetes Care 26:441-5, 2003. 5 pages.

Randolph AL, Nelson M, Akkapeddi S, Levin A Alexandrescu R. Reliability of measurements of pressures applied on the foot during walking by a computerized insole sensor system. Arch Phys Med Rehabil 81:573-8, 2000. 6 pages.

Robertson DG, Winter DA. Mechanical energy generation, absorption and transfer amongst segments during walking. J. of Biomechanics 13:845-854. 1980. 12 pages.

Rosenbaum D, Hautman S, Gold M, Claes L. Effects of walking speed on plantar pressure patterns and hindfoot angular motion. Gait Posture 2:191-7, 1994. 8 pages.

Rugg SG, Gregor RJ, Mandelbaum BR, Chie L. In vivo moment arm calculations at the ankle using magnetic resonance imaging (MRI). J Biomechanics 1990;23:495-501. 7 pages.

Sammarco GJ, Burnstein AH, Frankel VH. Biomechanics of the Ankle: a kinematic study. Orthop Cl N Amer 1973;4 (1):75-96. 11 pages.

Sangeorzan B, Sidles J. Hinge like motions of the ankle and subtalar articulations. Orthopaedic Transactions 1995;19 (2):331-332. 3 pages.

Sapega A A. Muscle performance evaluation in orthopaedic practice. J Bone Joint Surg 72-A: 1562-1574, 1990. 14 pages.

Segal A, Rohr E, Orendurff M, Shofer J, O'Brien M, Sangeorzan B. The effect of walking speed on peak plantar pressure. Foot Ankle Int. 25:926-33, 2004. 8 pages.

Simon SR, Mann RA, Hagy JL, Larsen LJ. Role of the Posterior Calf Muscles in Normal Gait. J Bone J Surg 60A, 465-472, 1978. 8 pages.

Skinner SR, Antonelli D, Perry J, Lester DK. Functional Demands on the Stance Limb in Walking; Orthopedics 8:355-361. 1985. 8 pages.

Soames RW, Foot Pressure Patterns During Gait. J. Biomed. Eng. 7:120-126. 1985. 7 pages.

Soames RW, Stott JRR, Goodbody A, Blake CD, Brewerton DA. Measurement of Pressure Under the Foot During Function. Med. Biol. Eng. Comput. 20:489-495. 1982. 8 pages.

Somers DL, Hanson JA, Kedzierski CM, Nestor KL, Quinlivan KY. The Influence of Experience on the Reliability of Goniometric and Visual Measurement of Forefoot Position. J Orthop Sports Phys Ther 1997;25:192-202. 11 pages.

Spoor CW, van Leeuwen JL, Meskers CG, Titulauer AF, Huson A. Estimation of instantaneous moment arms of lower-leg muscles. J Biomechanics 1990;27:1247-1259. 13 pages.

Stagni R, Leardini A, Catani F, Cappello A. A new semi-automated measurement technique based on X-ray pictures for ankle morphometry. J Biomechanics 2004;37:1113-1118. 6 pages.

Stähelin T, Nigg BM, Stefanyshyn DJ, van den Bogert AJ, Kim SJ. A method to determine bone movement in the ankle joint complex in vitro. J Biomechanics 1997;30(5)513-515. 4 pages.

Stauber WT. Eccentric Action of Muscles: Physiology, Injury, and Adaptation. Exercise and sport science reviews 17 157-185, 1989. 15 pages.

Stokes VP, Andersson C, Forssberg H. Rotational and translational movement features of the pelvis and thorax during adult human locomotion. Journal of Biomechanics 22:43-50, 1989. 10 pages.

Sutherland DH, An Electromyographic Study of the Plantar Flexors of the Ankle in Normal Walking on the Level. J. Bone J. Surg. 48:66-71, 1966. 6 pages.

Sutherland DH, Cooper L, Daniel D. The role of ankle plantar flexors in normal walking. J Bone Joint Surg, 42-A:354-363, 1980. 10 pages.

Thorstensson A, Grimby G, Karlsson J. Force-velocity relations and fiber composition in human knee extensor muscles. J Appl Physiol 40:12-16, 1976. 7 pages.

Warren GL, Maher RM, Higbie EJ. Temporal patterns of plantar pressures and lower-leg activity during walking:effect of speed. Gait Posture '9:91-100, 2004. 10 pages.

Weaver K, Price R, Czerniecki, Sangeorzan B Design and Validation of an Instrument Package Designed to Increase the Reliability of Ankle Range of Motion Measurements. Journal of Rehabilitation Research and Development, 38: 2001. 5 pages.

Wickiewicz TL, Roy RR, Posell PL, and Edgerton, VR.: Muscle architecture of the human lower limb. Clin. Orthop. Rel. Res. , 179:275-283, 1983. 9 pages.

Wilmore JH. Alterations in strength, body composition, and arthropometric measurements consequent to a 10-week weight training program. Med Sci Sports Exerc 6:133-138, 1974. 7 pages.

Winter DA. Energy generation and absorption at the ankle and knee during fast, natural and slow cadences. Clinical Orthopedics 175:147-154, 1983. 8 pages.

Xu H, Akai M, Kakurai S, Yokota K, Kaneko, H. Effect of Shoe Modifications on the Center of Pressure and In-Shoe Plantar Pressures. Am J Phys Med Rehabil. 6:516-24. 1999. 1 page.

Ying N, Kim W. Use of dual Euler angles to quantify the three-dimensional joint motion and its application to the ankle joint complex. J Biomechanics 2002;35:1647-1657. 11 pages.

Zhu H, Wertsch JJ, Harris GF, Alba M, Walking cadence effect on plantar pressure. Arch Phys.Med. Rehabil., 76:1000-5, 1995. 6 pages.

Grieve DW. Monitoring Gait. B.J. Hop Med, 2413:198-204, 1980. 6 pages.

Hettinger T and Muller E. (1953). Muscle capacity and muscle training Arbeits Physiol 15, 111-126. Original Paper in German. 10 pages.

Perrin DH. Reliability of isokinetic measures. Athletic Training 21:319-321, 1986. 3 pages.

Singh M, Karpovich PV. Isotonic and isometric forces of forearm flexors and extensors. J Appl Physiol 21:1435-1437, 1966. 5 pages.

Strizak AM, Gleim GW, Sapega A, Nicholas JA. Hand and forearm strength and its relation to tennis. Am J Sport Med 11: 234-239, 1983. 7 pages.

Parotec Plantar Pressure Measurement System page at www.londonorthotics.co.uk/loc-technology/foot-pressure.html, downloaded Mar. 3, 2009. 1 page.

Home page, www.rsscan.co.uk/, downloaded Mar. 3, 2009. 1 page.

System page, www.rsscan.co.uk/systems.php, downloaded Mar. 3, 2009. 1 page.

TOG GaitScan page at www.theorthoticgroup.com/TOG-TOG-GaitScan.html, downloaded Mar. 3, 2009. 1 page.

Hosein R, Lord M. A study of in-shoe plantar shear in normals. Clin. Biomechanics 15:46-53, 2000. 7 pages.

Katoh, Y, et al: Biomechanical analysis of foot function during gait and clinical applications. Clin Orthop Rel Res 177:22-23, 1983. 11 pages.

* cited by examiner

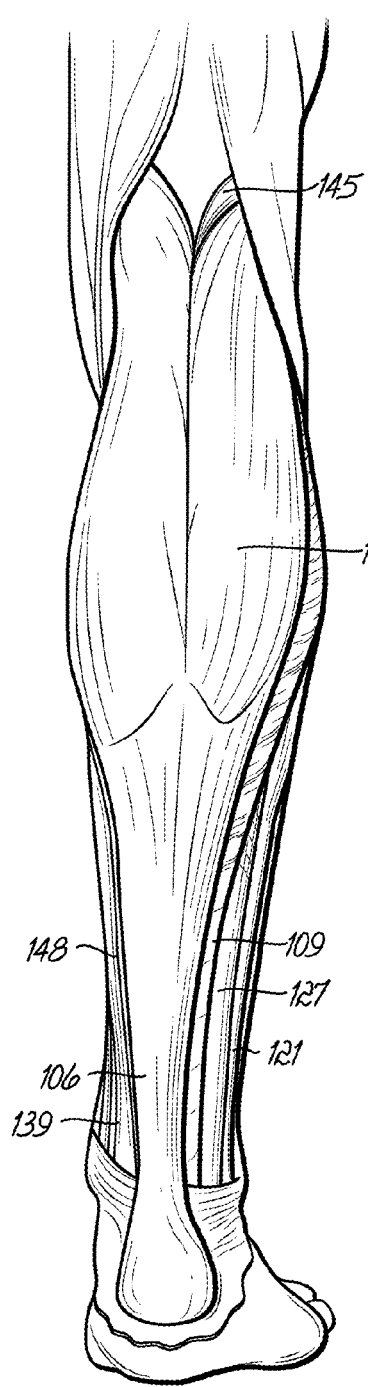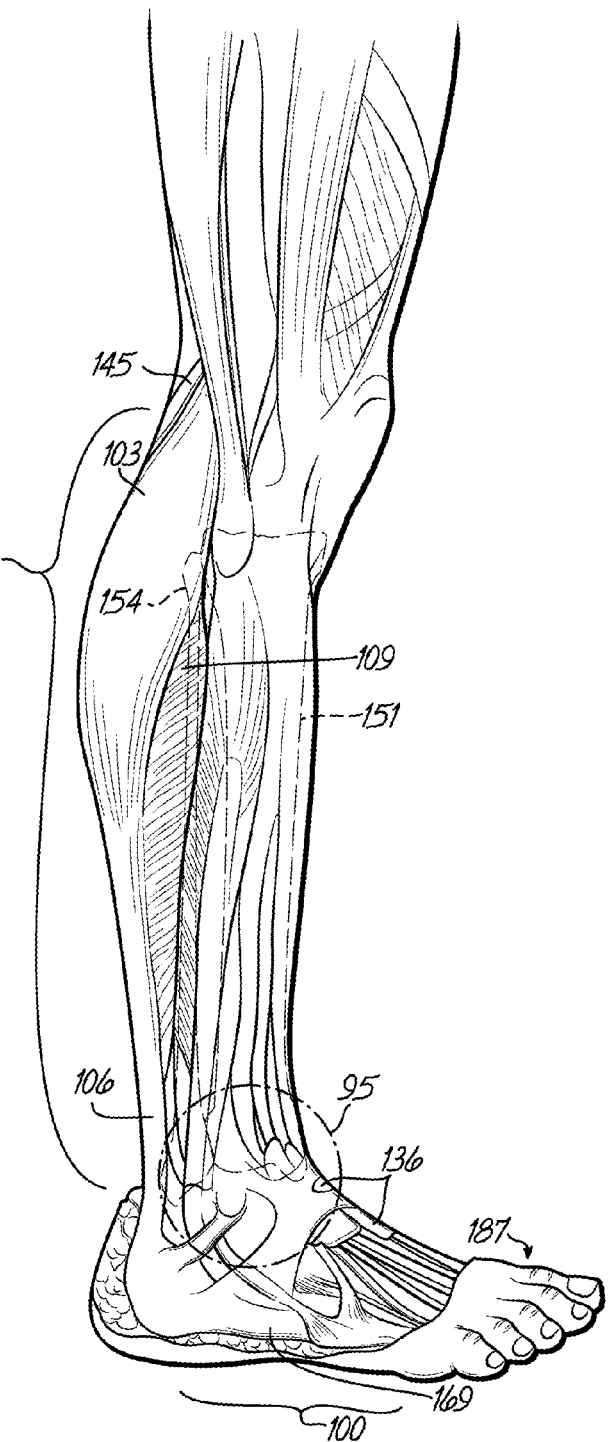
FIG. 3
FIG. 4

MUSCLE STRENGTH ASSESSMENT SYSTEM

PRIORITY CLAIM

This application claims benefit of priority of U.S. non-provisional application Ser. No. 11/457,959 titled "MUSCLE STRENGTH ASSESSMENT SYSTEM" filed Jul. 17, 2006, whose inventor is Jeffrey Arthur Oster. The non-provisional application Ser. No. 11/457,959 claims priority of U.S. provisional application Ser. No. 60/699,839 titled "CT Band Syndrome and the CT Band Index" filed Jul. 15, 2005, whose inventor is Jeffrey Arthur Oster. This application also claims priority to U.S. provisional application Ser. No. 60/699,839. All of these applications are incorporated herein by reference in their entirety and for all purposes.

FIELD OF THE INVENTION

The invention generally relates to assessing muscle strength, and more particularly, using computer implemented processes to assess the strength of muscles comprising the leg, ankle, and foot.

BACKGROUND OF THE INVENTION

Walking is generally a unique orchestration of three physical properties: force, resistance and balance. Sustained walking may require that these functions occur over and over in the course of a day. The leg, ankle and foot are generally the terminus of all forces generated in the act of walking. If the forces applied to the leg, ankle and foot become too great, injury occurs. Some of the techniques used by researchers, clinicians and/or surgeons for assessing muscle strength of the leg, ankle, and/or foot are discussed hereinbelow.

Some traditional techniques available to clinicians and surgeons (e.g., podiatrist and orthopedic surgeons) for assessing conditions and defining treatment plans for their patients do not take into account the mechanical interaction between the leg, ankle, and foot, which may increase the difficulty of diagnosing and/or treating patients. As an example, clinicians have traditionally approached the ankle as a simple hinge joint and have evaluated the ankle by measuring equinus. Typically, the methods used to measure equinus focus on the range of motion of the ankle as defined by the relationship between the long axis of the foot and the long axis of the leg. Equinus may be present if dorsiflexion (i.e., bending backward) of the foot at the ankle is limited to less than ten degrees when the subtalar joint is in the neutral position and the midtarsal joint is maximally pronated. But, some clinicians and researchers have found that measuring equinus can be subjective and difficult to duplicate based upon variations in training and testing techniques. For instance, the lack of uniformity may make it difficult to determine whether surgical lengthening of the Achilles Tendon is appropriate. Moreover, measuring equinus may measure the range of motion of the ankle, but it does not measure the mechanical function of the leg, ankle and foot.

As a result, to understand the physical properties of the forces that occur during the act of walking, the leg ankle and foot should be discussed as a lever arm as these physical properties are predominately controlled by a lever arm made up of the leg, ankle and foot. However, this lever arm carries sustained loads that have been typically difficult to quantify and illusive to researchers who employ direct physical measurements. Subsequently, when clinicians and surgeons try to assess the function of this lever arm, they may be unable to use a reliable measurement of its function, which may hinder diagnosis and/or treatment of patients. Numerous attempts have been made to assess the lever arm of the leg, ankle and foot in a research setting using direct measurements, but a method applicable in a clinical setting has generally not been established. Therefore, clinicians may be unable to quantitatively assess the mechanical function of this lever arm.

In particular, critical to a discussion of lever arms are the specific characteristics of the lever arm such as the length, the location, and the center of load. The ability to quantify these physical properties of the lever arm would enable a direct measurement of the lever arm. Numerous studies have been performed to define the specific lever arm characteristics of the ankle. One study noted that surgical placement of transducers would be required to monitor direct pressure. As such, although some direct measurement studies have been performed to define the specific lever arm characteristics of the ankle, the majority of these studies are hard to interpret and are generally difficult to duplicate in a clinical setting. Moreover, a study described measuring force delivered to bone joints and ligaments as direct and indirect. Thus, indirect models may be required to measure living structures.

Another conventional technique measures the force of one muscle against another muscle, referred to as muscle strength ratios, by measuring the relationship between two reciprocal muscles, an agonist and an antagonist. Muscle strength ratios have traditionally been measured using apposing muscle groups. As an example, muscle strength ratios are commonly used to measure the hamstrings and quadriceps and this measurement creates a ratio of the muscle function of the knee. The relationship between the two muscles is generally that of eccentric vs concentric muscle action. Muscle strength ratios may also be described by a number of different names including agonist/antagonist ratios, concentric/eccentric ratios, reciprocal contraction mode ratios and/or reciprocal muscle group ratios.

Muscle strength ratios may be measured using static or dynamic muscle testing. Static muscle testing, or isometric contraction of muscle may be created when muscle is contracted with no change in the muscle's length. Isometric dynamometry measures the maximal center of pressure (COP). Maximal isometric COP measurements (or isometric dynamometry) may be performed by a number of different commercially available products. However, generally, only a limited focus of data is measured by isometric dynamometry. As such, isometric dynamometry may simply give a snapshot of the function of a lever arm, recording the maximal force generated by the lever arm.

On the other hand, dynamic muscle testing, or isokinetic dynamometry, measures the moment (torque) of a lever arm as resistance is applied at a constant speed. Isokinetic dynamometry may measure peak torque, angle specific torque, work (work=torque·times·distance), power, the rate of torque production and torque acceleration energy. Peak torque, with a relationship to the angle of the joint, is a commonly used isokinetic measure. Isokinetic assessment typically requires expensive equipment that is not readily available to most clinicians. Moreover, although an isokinetic assessment may be a more comprehensive record of the entire range of motion of a lever arm, the validity, reproducibility and clinical significance of the measures are often times questionable due to lack of standardization. As such, isokinetic dynamometry is generally used for testing muscle strength ratios in the research community but not widely used by clinicians in a clinical practice.

Several researchers have also attempted to define the percentage of load delivery by individual muscle and tendon units of the lever arm. The general rule of thumb is that a muscle's potential for work is directly proportional to the cross section of the muscle. While the contribution of each muscle and tendon unit may be defined in a lab setting, clinical application of this testing has also generally been difficult to accomplish.

A need therefore exists for a muscle strength measurement of the lever arm that may be used in a clinical setting.

SUMMARY OF THE INVENTION

The invention addresses these and other problems associated with the prior art by providing an apparatus and methods that generate, receive, and/or utilize a value that is indicative of muscle strength of the lever arm comprising the leg, ankle, and foot. The value will be referred to herein as a CT Band Index. The lever arm comprises the anatomical structures of the leg, ankle, and foot, and will be referred to herein as the CT Band with the "C" generally referencing the calf and the "T" generally referencing the toes. The CT Band Index may be generated, received, and/or utilized manually by a user (e.g., a clinician, etc.), automatically via a computer and/or apparatus, or by a combination of manual and automatic. Generally, the CT Band Index is a technique that may be used in a clinical as well as in a research setting, and may be duplicated.

These and other advantages and features, which characterize the invention, are set forth in the claims annexed hereto and forming a further part hereof. However, for a better understanding of the invention, and of the advantages and objectives attained through its use, reference should be made to the Drawings, and to the accompanying descriptive matter, in which there is described exemplary embodiments of the invention.

BRIEF DESCRIPTION OF THE DRAWINGS

FIG. 3 is a back side elevation view of the CT Band.

FIG. 4 is a right side elevation view of the CT Band.

DETAILED DESCRIPTION

Figure 1:
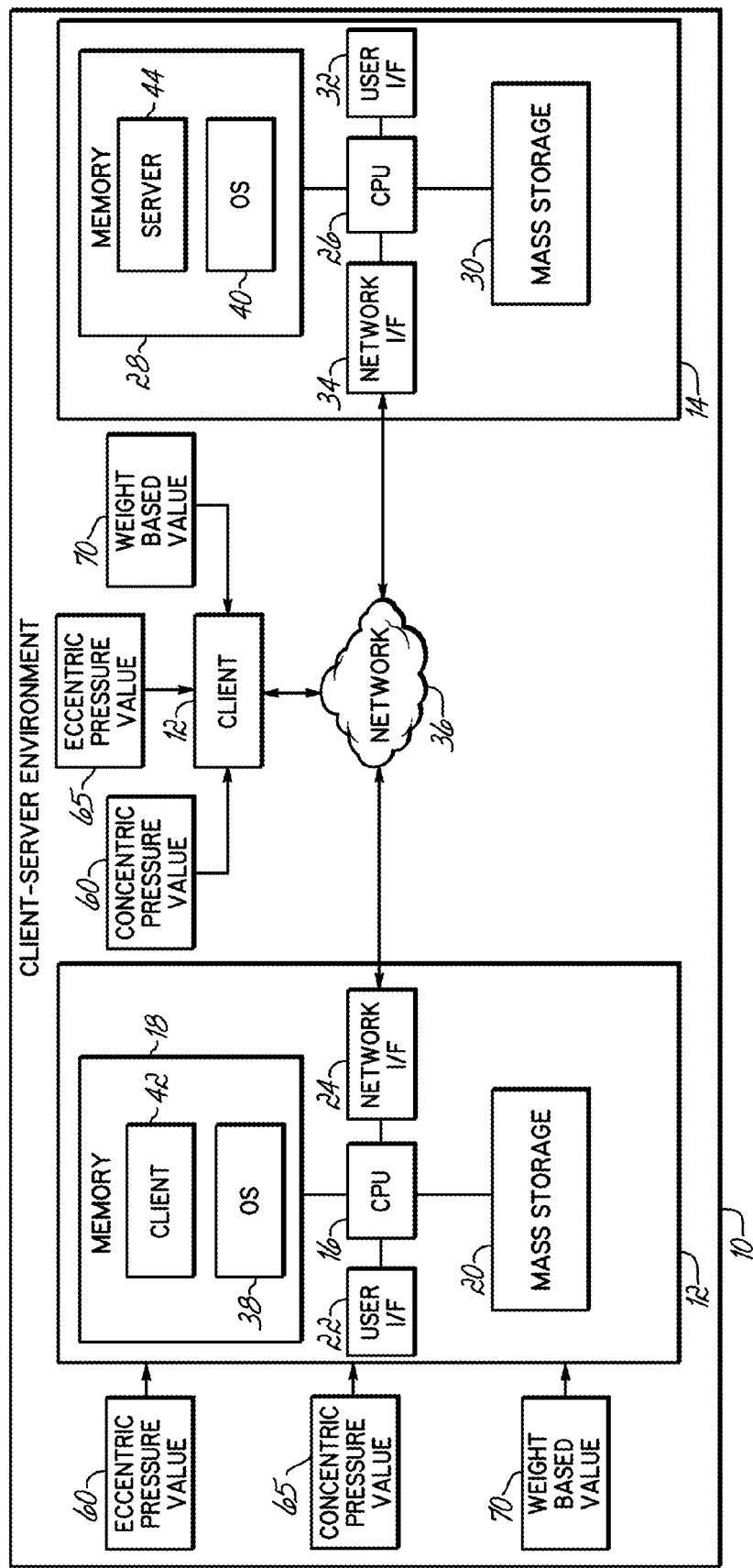
FIG. 1 is a block diagram of a client-server environment consistent with the invention.

The embodiments discussed hereinafter generate, receive, and/or utilize a CT Band Index of a CT Band of a patient. A CT Band Index may be practically any value that is indicative of muscle strength of the lever comprising the leg, ankle, and foot. Additionally, the term muscle and muscle strength are used for simplicity herein but it should be understood that the terms may not be limited to only muscles (e.g., muscle strength may not be limited to the strength of muscles only). Furthermore, in some embodiments, the CT Band Index may provide normative data that takes into consideration differences between patients and attempts to adjust for these differences (e.g., height, weight, strength, and muscle stature). However, normative data need not be provided by the CT Band Index consistent with the principles of the present invention.

Additionally, in some embodiments, the CT Band Index may be indicative of non-reciprocal muscle strength of the CT Band as the same group of muscles of the CT Band may provide negative and positive work. In other words, the CT Band Index may measure the positive and negative force of the same muscle or muscle group (e.g., CT Band) instead of a reciprocating or antagonistic muscle or muscle group. As such, the CT Band Index may not measure two antagonistic muscles, but instead measures the concentric, or positive, and eccentric, or negative, muscle contraction of the same muscle group. In particular, although a muscle may have an antagonist, a lever arm may not take into consideration motion in two directions, and instead, the focus of a lever arm is on how to gain mechanical advantage using force to move load. As a result, the same group of muscles may provide negative and positive work in the same lever arm.

As such, the CT Band Index may be a muscle strength index that measures the lever arm function of the CT Band as oppose to measuring the strength of an isolated muscle or antagonistic muscles. Moreover, the CT Band Index may be indirectly indicative of non-reciprocal muscle strength of the CT Band. For instance, the CT Band Index may not measure two antagonistic muscles or reciprocating muscles but instead measures the positive and negative force of the same muscle or muscle group (e.g., CT Band) and this may be thought of as non-reciprocating and/or non-antagonistic. When both the positive and negative work of a single muscle or muscle group is measured and related in a mathematical formula, this may be referred to herein as an anisotropic non-reciprocal muscle strength measurement. This non-reciprocal muscle strength measurement may be generated by determining an eccentric pressure value and a concentric pressure value and generating a value indirectly indicative of the non-reciprocal muscle strength. The value indicative of non-reciprocal muscle strength of the CT Band may be generated by summing the eccentric and concentric values together as oppose to dividing the eccentric and concentric pressure values, which may be indicative of a reciprocating muscle strength measurement. Furthermore, the sum may be multiplied by a weight based value. As this may be done external to the body of a patient and/or does not measure each individual muscle directly, this may be considered an indirect measurement and thus an indirect non-reciprocal muscle strength measurement.

Additionally, in some embodiments, the CT Band Index may provide normative data with strength differences between individuals normalized when related to relative body size. As such, the CT Band Index may be generated from one or more eccentric pressure values, one or more concentric pressure values, and one or more weight based values. Generally, the CT Band may employs balance of the use of concentric and eccentric contraction of skeletal muscle.

An eccentric pressure value may be practically any value indicative of an eccentric contraction. An eccentric pressure value may be determined from an eccentric contraction, also called a negative contraction, negative work, lengthening contraction, and/or decelerator muscle function. An eccentric contraction may occur when a muscle performs work such as carrying a load while lengthening. Resistance to muscle lengthening of the CT Band may be thought of as eccentric or negative force.

A concentric pressure value may be practically any value indicative of a concentric contraction. A concentric pressure value may be determined from a concentric contraction, also called a positive contraction. A concentric contraction may occur when a muscle shortens against a load. Active muscle contraction with muscle shortening of the CT Band may be thought of as concentric or positive force.

A weight based value may be practically any value that is includes a weight measurement. For instance, a weight based value may simply be the weight of a patient, or may comprise the BMI of a patient, which may be determined by the weight and height of the patient.

Figure 5:
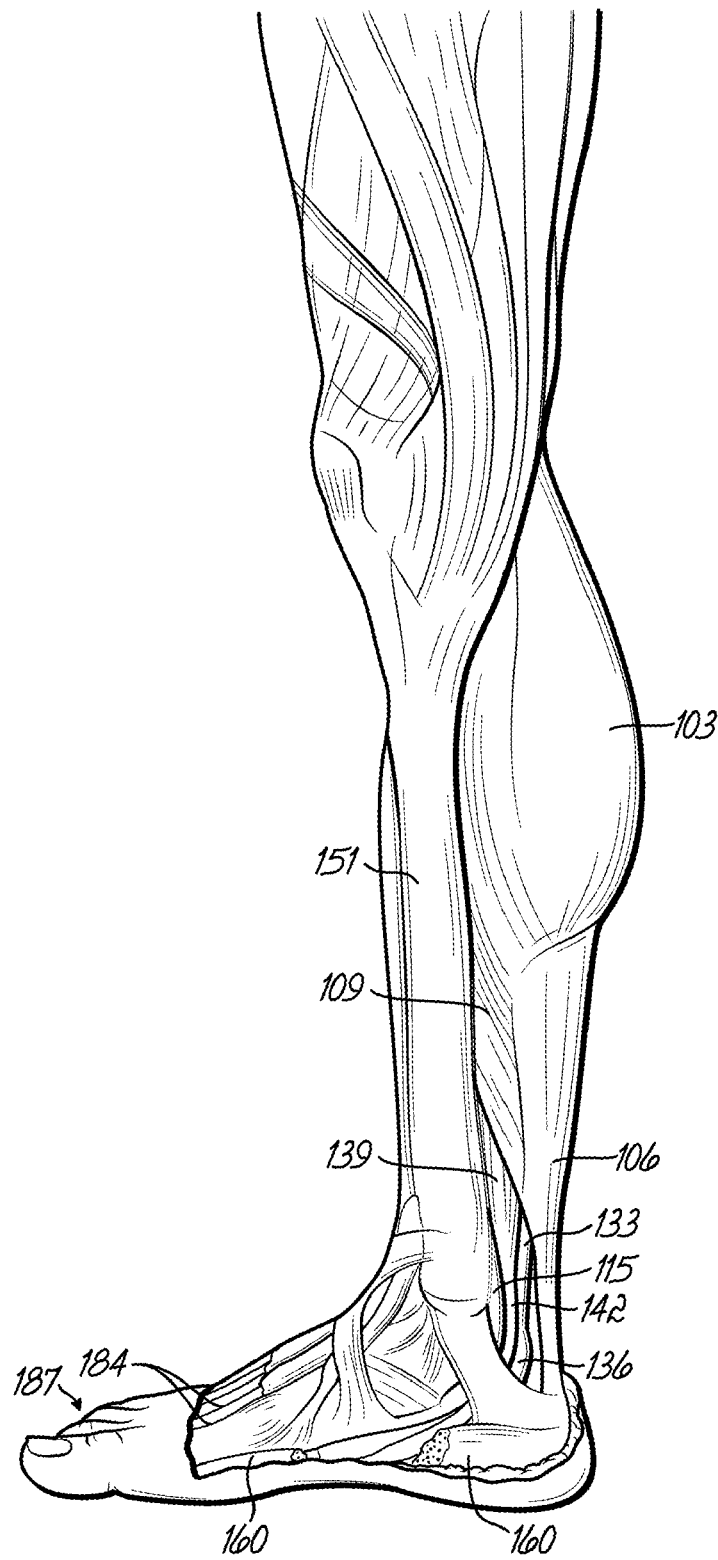
FIG. 5 is a left side elevation view of the CT Band.

The CT Band is generally depicted in FIGS. 3, 4, and 5. The CT Band is a lever arm comprising the leg, ankle and foot. The CT Band may include at least a portion of the leg, at least a portion of the ankle, at least a portion of the foot, and/or a any combination or portion thereof. The CT Band may even be from about a portion of the leg such as about a calf of the leg or proximal to the knee of the leg to about a forefoot of the leg. The forefoot may include at least one toe. The CT Band may have an Effort Arm 90 which may be at least a portion of the leg, a Resistance Arm 100 which may be at least a portion of the foot, and a Fulcrum 95 which may be at least a portion of the ankle. Although not all of the structures of the CT Band are illustrated in FIGS. 3, 4, and 5, one of ordinary skill in the art will appreciate that other structures, such as those mentioned below, are also part of the CT Band. Generally, the CT Band is comprised of muscles, bones, cartilage, and tendons Structures of the Effort Arm of the CT Band may include the extrinsic plantarflexors, such as (1) the gastrocnemius muscle 103 and Achilles tendon 106, (2) the soleus muscle 109 and Achilles tendon 106 (3) the posterior tibial muscle 115 and tendon (4) the peroneus longus muscle 121 and tendon (5) the peroneus brevis muscle 127 and tendon (6) the flexor hallucis longus muscle 133 and tendon 136, (7) the flexor digitorum longus muscle 139 and tendon 142, and (8) the plantaris muscle 145 and tendon 148. Additional Effort Arm structures may include (9) the tibia 151 and fibula 154, and (10) the gastrocnemius aponeurosis.

Structures of the Resistance Arm of the CT Band may include the intrinsic musculature of the foot such as (1) the abductor hallucis 160, (2) the flexor digitorum brevis, (3) the flexor hallucis brevis, (4) the abductor digiti minimi 169, and (5) the quadratus plantae. Additional Resistance Arm structures may include ligaments such as (6) the Periarticular ligaments, and (7) the spring ligament, and (8) the plantar fascia, and (9) bones 184 and joints 187 of the foot. In comparison to the Effort Arm, the Resistance Arm of the CT Band is an anatomically diverse structure composed of muscle, fascia, tendon, bone and joints.

The Fulcrum of the CT Band may be the joint axis of the talo-crual joint with the axis of the talo-crual joint constantly changing position during the range of motion of the ankle in gait.

Turning now to the remaining Drawings, wherein like numbers denote like parts throughout the several views, FIG. 1 illustrates a client-server system, or environment 10. Environment 10 includes at least one apparatus, e.g., one or more client computers 12 and/or one or more server computers 14. For the purposes of the invention, each computer 12, 14 may represent practically any type of computer, computer system or other programmable electronic device capable of functioning as a client and/or server in a client-server environment. Moreover, each computer 12, 14 may be implemented using one or more networked computers, e.g., in a cluster or other distributed computing system. Moreover, as is common in many client-server systems, typically multiple client computers 12 will be interfaced with a given server computer 14.

Computer 12 typically includes a central processing unit 16 including at least one microprocessor coupled to a memory 18, which may represent the random access memory (RAM) devices comprising the main storage of computer 12, as well as any supplemental levels of memory, e.g., cache memories, non-volatile or backup memories (e.g., programmable or flash memories), read-only memories, etc. In addition, memory 18 may be considered to include memory storage physically located elsewhere in computer 12, e.g., any cache memory in a processor in CPU 16, as well as any storage capacity used as a virtual memory, e.g., as stored on a mass storage device 20 or on another computer coupled to computer 12. Computer 12 may also contain a database management system (DBMS) to interface with a database. The DBMS and database may both be in memory 18, or the database may be in mass storage 20, or the DBMS and/or database may be in other locations.

Computer 12 also typically receives a number of inputs and outputs for communicating information externally. For interface with a user or operator, computer 12 typically includes a user interface 22 incorporating one or more user input devices (e.g., a keyboard, a mouse, a trackball, a joystick, a touchpad, and/or a microphone, among others) and a display (e.g., a CRT monitor, an LCD display panel, and/or a speaker, among others). Otherwise, input and user input may be received via another computer or terminal wirelessly or via wires. Computer 12 may receive as an input an eccentric pressure value 60, concentric pressure value 65, and weight based value 70, and/or a CT Band Index.

For additional storage, computer 12 may also include one or more mass storage devices 20, e.g., a floppy or other removable disk drive, a hard disk drive, a direct access storage device (DASD), an optical drive (e.g., a CD drive, a DVD drive, etc.), and/or a tape drive, among others. Furthermore, computer 12 may include an interface 24 with one or more networks (e.g., a LAN, a WAN, a wireless network, and/or the Internet, among others) to permit the communication of information with other computers and electronic devices. It should be appreciated that computer 12 typically includes suitable analog and/or digital interfaces between CPU 16 and each of components 18, 20, 22 and 24 as is well known in the art.

In a similar manner to computer 12, computer 14 includes a CPU 26, memory 28, mass storage 30, user interface 32 and network interface 34. However, given the nature of computers 12 and 14 as client and server, in many instances computer 14 will be implemented using a multi-user computer such as a server computer, a midrange computer, a mainframe, etc., while computer 12 will be implemented using a desktop or other single-user computer. As a result, the specifications of the CPU's, memories, mass storage, user interfaces and network interfaces will typically vary between computers 12 and 14. Computer 14 may also have a DBMS and/or database. Other hardware environments are contemplated within the context of the invention.

Computers 12, 14 are generally interfaced with one another via a network 36, which may be public and/or private, wired and/or wireless, local and/or wide-area, etc. Moreover, network 36 may represent multiple, interconnected networks. In the illustrated embodiment, for example, network 36 may include the Internet.

Each computer 12, 14 operates under the control of an operating system 38, 40, and executes or otherwise relies upon various computer software applications, components, programs, objects, modules, data structures, etc. (e.g. client 42 and server 44). Moreover, various applications, components, programs, objects, modules, etc. may also execute on one or more processors in another computer coupled to computer 12, 14 via a network, e.g., in a distributed or client-server computing environment, whereby the processing required to implement the functions of a computer program may be allocated to multiple computers over a network.

In general, the routines executed to implement the embodiments of the invention, whether implemented as part of an operating system or a specific application, component, program, object, module or sequence of instructions, or even a subset thereof, will be referred to herein as "computer program code," or simply "program code." Program code typically comprises one or more instructions that are resident at various times in various memory and storage devices in a computer, and that, when read and executed by one or more processors in a computer, cause that computer to perform the steps necessary to execute steps or elements embodying the various aspects of the invention. Moreover, while the invention has and hereinafter will be described in the context of fully functioning computers and computer systems, those skilled in the art will appreciate that the various embodiments of the invention are capable of being distributed as a program product in a variety of forms, and that the invention applies equally regardless of the particular type of computer readable media used to actually carry out the distribution. Examples of computer readable media include but are not limited to tangible recordable type media such as volatile and non-volatile memory devices, floppy and other removable disks, hard disk drives, magnetic tape, optical disks (e.g., CD-ROMs, DVDs, etc.), among others, and transmission type media such as digital and analog communication links.

In addition, various program code described hereinafter may be identified based upon the application within which it is implemented in a specific embodiment of the invention. However, it should be appreciated that any particular program nomenclature that is used herein is used merely for convenience, and thus the invention should not be limited to use solely in any specific application identified and/or implied by such nomenclature. Furthermore, given the typically endless number of manners in which computer programs may be organized into routines, procedures, methods, modules, objects, and the like, as well as the various manners in which program functionality may be allocated among various software layers that are resident within a typical computer (e.g., operating systems, libraries, API's, applications, applets, etc.), it should be appreciated that the invention is not limited to the specific organization and allocation of program functionality described herein.

A server 44 may generally be considered to include any program code resident on a computer or other programmable electronic device that is capable of servicing such requests in a distributed computer system. It should also be appreciated that an server 44 in this context may be resident on the same computer as the client 42, (e.g., in the peer to peer system 11 described hereinabove), or in the alternative, the server 44 may be resident on an intermediate computer coupled between the client(s) (e.g., as illustrated in client-server system 10). A client 42 may generally be considered to include any program code resident on a computer or other programmable electronic device that is capable of making requests of another computer in a distributed computer system. Additionally, client 42 and server 44 may be considered to include the hardware associated with each (e.g., client computer 12 and server computer 14, respectively) as well as the software (e.g., program code). Furthermore, client 42 may be a web browser, an email client, instant messaging client, etc. and server 44 may be a web server, an email server, instant message server, etc.

Figure 2:
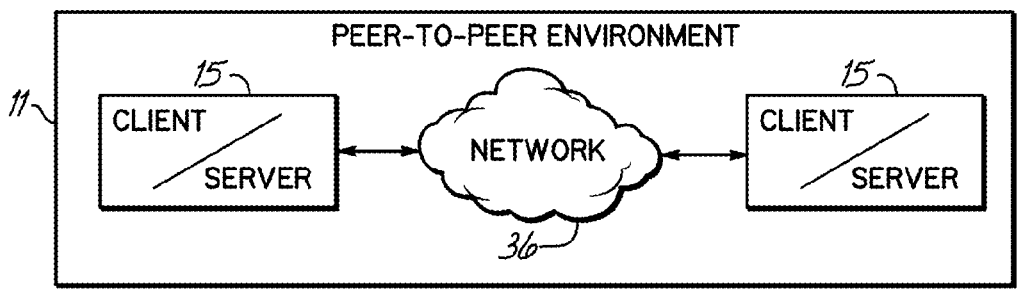
FIG. 2 is a block diagram of a peer to peer environment consistent with the invention.

FIG. 2 generally illustrates a peer to peer based computer system or environment 11 that may be used consistent with the invention. In particular, the peer to peer computer system 11 may have one or more peer computers 15 interfacing with one another via a network 36, which may be public and/or private, wired and/or wireless, local and/or wide-area, etc. Moreover, network 36 may represent multiple, interconnected networks. In the illustrated embodiment, for example, network 36 may include the Internet. Generally, each peer computer 15 may act as both a client 12 and/or a server 14 as generally described by like numbers in connection with FIG. 1.

Those of ordinary skill in the art will appreciate that a combination of client-server environment 10 and peer to peer environment 11 may also be used. Moreover, a computer 12, 14 may but need not interface with another computer 12 or computer 14. Furthermore, computer 12 need not be a client computer and/or computer 14 need not be a server computer. Moreover, those skilled in the art will recognize that the exemplary environments illustrated in FIGS. 1 and 2 are not intended to limit the present invention. Indeed, those skilled in the art will recognize that other alternative hardware and/or software environments may be used without departing from the scope of the invention.

Furthermore, for the purposes of the invention, an apparatus may represent practically any type of computer, computer system or other programmable electronic device, including a client computer 12, a server computer 14, a portable computer, a handheld computer, an embedded controller, etc. Moreover, an apparatus may be implemented using one or more networked computers, e.g., in a cluster or other distributed computing system. Apparatus will hereinafter also be referred to as a "computer," although it should be appreciated that the term "apparatus" may also include other suitable programmable electronic devices consistent with the invention.

As noted above, embodiments consistent with the invention are generally configured to generate, receive, and/or utilize a CT Band Index of a CT Band of a patient. For instance, computer 12 may receive an eccentric pressure value 60 input, concentric pressure value 65 input, and weight based value 70 input and generate the CT Band Index utilizing the values. A user may input the values using a keyboard, alternatively, computer 12 may interface with at least one sensor and the sensor may be programmed to transmit the values to computer 12 and/or computer 12 may request the values from the sensor. A sensor may interface wirelessly or via wires using conventional techniques with computer 12 or may even be attached to computer 12 via a wire. Computer 12 may be a stationary computer, hand-held computer, etc. Once computer 12 generates the CT Band Index, this CT Band Index may be stored locally (e.g., in a database) to collect lever arm related data also referred to as herein as CT Band related data.

CT Band related data or lever data as used herein may include at least one other CT Band Index of the same patient or other patients, may include diagnoses, may include treatments, may include statistical information (e.g., age, the presence or lack of conditions that may affect the CT Band such as diabetes, etc.), may include progress information, may include medical histories, etc. CT Band related data or lever arm related data may be practically any data that is associated with the CT Band that can be generated either manually (e.g., by a clinician) or automatically (e.g., by a computer).

CT Band related data may be collected by computer 12 and/or may be collected by another computer 12 or 14. For instance, the generated CT Band Index may be transmitted via the internet to a computer 14 which may receive a CT Band Index from computer 12 and/or CT Band related data collected by computer 12 and add it a collection of CT Band related data from around the world maintained by computer 14. Computer 14 may have a web portal, website, etc., for example, stored on it and users (e.g., clinicians) may send data to or receive data from (e.g., displayed on a user's computer 12) from computer 14 via the web portal, website, etc. Nonetheless, computer 12 or computer 14 may compare the generated CT Band Index to the CT Band related data, which may be stored in a database in memory, etc. A diagnosis and/or treatment may be determined by computer 12 and/or 14 and this diagnosis and/or treatment may be output. The diagnosis and/or treatment may be determined, for example, from a database of diagnoses and/or treatments previously determined by clinician, etc. As an example, the web site may serve as a clearing house of sorts for CT Band related data, with the providers and/or clinicians participating in studies where they would submit data to be pooled. In this way, CT band testing may be employed to develop large pools of data. This website may also be a repository for CT Band related data, analysis, research, and/or papers. To participate in this web based project, providers and/or clinicians may first need to be certified, trained, and/or instructed on the background and testing methods.

Those of ordinary skill in the art will appreciate that some or all of the functionality described above may be performed manually by a user (e.g., a clinician). Furthermore, a method of teaching a user, for example, by instructional material is contemplated within the scope of the present invention. For instance, instructional material indicating how some or all of the functionality may be performed. Similarly, instructional material prompting a user to perform some or all of the functionality is contemplated within the scope of the present invention. The instructional material may be part of a kit and may include, for example, one or more sensors. Additionally, it may also include one or more educational courses, a platform, a weight sensor (e.g., a scale), a height sensor (e.g., a tape measurer, height measuring scale, etc.), and/or handheld computer or apparatus. The computer may be able to output information and may have at least one wire or may interface wirelessly. It may also prompt the user to interpret the value, for example, compare it to CT Band related data.

Figure 6:
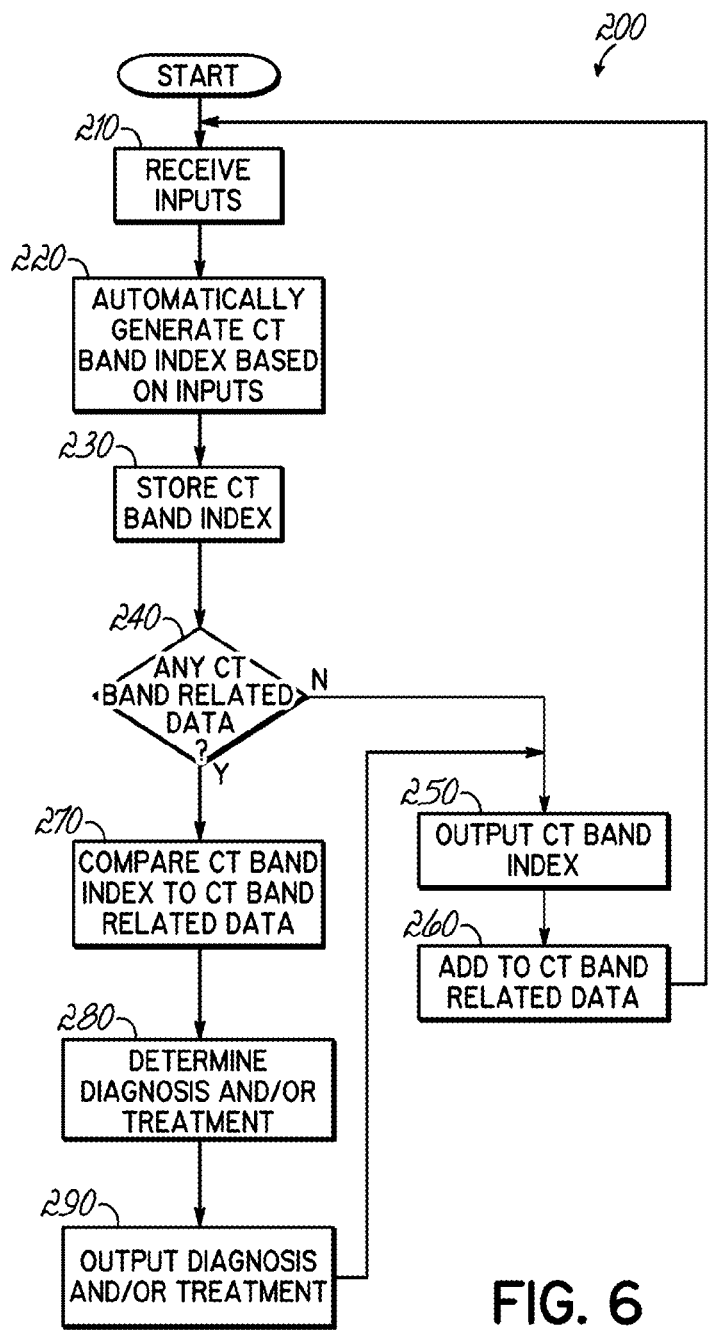
FIG. 6 is a flowchart of a generating a CT Band Index routine executed in an environment of FIGS. 1 and 2.

Turning next to FIG. 6, an exemplary generating a CT Band Index routine consistent with the principles of the present invention is shown. Routine 200 may be run by a computer or other apparatus, which may be handheld, stationary, etc. and/or connected to another computer. Practically any apparatus such as those described hereinabove capable of generating a CT Band Index may be used consistent with the present invention. Furthermore, the CT Band Index may be generated automatically, locally or remotely. For instance, a processor on a remote server may receive/determine the inputs, which may be input manually and locally by a user or automatically and locally by a computer, and the processor may automatically and remotely generate the CT Band Index. Furthermore, the CT Band Index may be generated automatically in its entirety or may be partially generated automatically. The CT Band Index may also be generated completely manually by a user (e.g., clinician, nurse, etc.) without the aid of a web portal, apparatus, computer, etc. Moreover, those of ordinary skill in the art may appreciate that practically all the techniques described herein, e.g., in connection with the CT Band Index and CT Band related data, may be performed partially manually, partially automatically, completely manually, or completely automatically, and/or by a combination of manual and automatic or automatic and manual. Furthermore, practically all the techniques described herein may be performed completely locally (e.g., all by a user, all by a local computer or apparatus), completely remotely (e.g., server receives inputs and generates CT Band Index and compares CT Band Index to CT Band related data), partially locally, partially remotely, and/or by a combination of local and automatic or automatic and local.

Turning to routine 200 in FIG. 6, block 210 receives at least one input. The inputs received in block 210 may be an eccentric pressure value, a concentric pressure value, and a weight based value. At least one eccentric pressure value input, at least one concentric pressure value input, and/or at least one weight based value input may be received in block 210. Those of ordinary skill in the art may appreciate that multiple eccentric pressure values, multiple concentric pressure values, and/or multiple weight based values may be received. As such, the average of the eccentric pressure values, the average of the concentric pressure values and/or the average of the weight based values may be determined and may be more reliable than a single eccentric pressure value, a single concentric pressure value and a single weight based value. Moreover, the average may be determined prior to receipt of the inputs and therefore one or more the received inputs may be an average. The inputs may be received from a computer, sensor, sensor attached the computer, manual input by a user, etc. How the inputs received in block 210 are determined will be discussed in greater detail in connection with routine 300 in FIG. 6 herein below.

Next, block 220 automatically generates a CT Band Index based on the inputs.
The CT Band Index may be generated by using a formula. The formula may read:

$$\text{CT Band Index} = (\text{eccentric pressure value/concentric pressure value}) \times \text{weight in lbs.} \text{ or CT Band Index} = (\text{average eccentric pressure value/concentric pressure value}) \times \text{weight in lbs.}$$

or $$\text{CT Band Index(BMI adjusted)} = \text{average eccentric pressure value/average concentric pressure value}) \times \text{BMI}$$

or any combination or portion thereof.
The formula may read:

$$\text{CT Band Index} = (\text{Concentric pressure value} + \text{Eccentric pressure value}) \times \text{Weight based value.}$$

In one preferred embodiment, the formula reads:

$$\text{CT Band Index} = (\text{Concentric mCOP} + \text{Eccentric mCOP}) \times \text{Weight in lbs.}$$

The term mCOP refers to the maximum center of pressure. The mCOP of the forefoot, which is part of the CT Band, may be beneath the second metatarsal head, which is generally about the second toe.

A formula consistent with the principles of the invention may read:

$$\text{CT Band Index(BMI adjusted)} = (\text{Concentric mCOP} + \text{Eccentric mCOP}) \times \text{BMI.}$$

BMI may be expressed as $$\text{BMI} = (\text{Weight in lbs.}/(\text{Height(in.)} \times \text{Height(in.)})) \times 703$$

The following formula may be used in an embodiment:

$$\text{CT Band Index(BMI adjusted)} = (\text{Average concentric mCOP} + \text{Average eccentric mCOP}) \times \text{BMI.}$$

Those of ordinary skill in the art will also appreciated that other variations may be made in the formula. In particular, any portion or combination thereof may be used. Furthermore, the x symbol stands for multiplication and the/symbol stands for division. For example, instead of the weight based value being expressed in weight in lbs., other weight measurements may be used such as weight in kilograms, etc. or a weight measurement may even be determined in a metric other than lbs. The measurement may then be converted to lbs. Furthermore, a modifier may be included in the formula.

Next, in block 230 the generated CT Band Index may be stored. The CT Band Index may be stored locally on a computer or on a handheld apparatus, etc. or remotely, for example on a server. The generated CT Band Index may also be stored as an entry for a patient in a database. As such, the generated CT Band Indexes for the patient may be monitored and tracked for changes. Furthermore, those of ordinary skill in the art may appreciate that generated CT Band Index may be stored to produce a collection of data such as the CT Band related data. CT band related data may be normative data which the generated CT Band Index may be compared to.

Turning next to block 240, block 240 determines whether there is any CT Band related data. The CT Band related data may be stored locally on a computer, handheld apparatus etc. or remotely on a server and may be accessed via a web portal. If there is no CT Band related data then the generated CT Band index may be output in block 250 (e.g., output on a display, readout, printout, etc.) and the generated CT Band Index may be used to start a collection of CT Band related data in block 260. Next, control passes to block 210 to receive more inputs. Those of ordinary skill in the art may appreciate that block 230 (as well as other blocks in routine 200) may be optional in some embodiments. For example, although the generated CT Band Index may be separately stored as depicted in routine 200, the generated CT Band Index may be simply added to CT Band related data as indicated in block 260.

Returning to block 240, if there is CT Band related data then block 270 compares the generated CT Band Index to the CT Band related data. The generated CT Band Index can be compared to identical CT Band Index in the CT Band related data to determine what data is available for that specific CT Band Index, as an example, or the generated CT Band Index can be compared to see if it falls below or above a normal CT Band, etc. In block 280, a diagnosis and/or a treatment may be determined (e.g., based upon diagnoses and/or treatments the CT Band related data indicates which treatments have been successful, which treatments decreased CT Band Indexes, which treatments increased CT Band Indexes, etc.) and may be output in block 290. Those of ordinary skill in the art should appreciate that the terms treating, treatment, and/or diagnosis may include preventive care, may include an indication that no treatment is necessary, etc. For instance, a comparison may indicate medical conditions that have occurred to patients with the a CT Band Index identical to or similar to the generated CT Band Index and a diagnosis and/or preventive treatment may be determined in block 280. Next, control passes to block 250 to output the generated CT Band Index and the generated CT Band Index is added to the CT Band related data in block 260. Next, control passes to block 210 to continue to receive inputs.

Those of ordinary skill in the art may appreciate that routine 200 is generally illustrated as one that may be automatically preformed by a computer, an apparatus (stationary, hand held, etc.), etc., however routine 200 may be adapted to be preformed manually. For instance, instead of automatically generating the CT Band Index based on the inputs, the inputs may be manually plugged into one of the formulas listed herein above and manually calculated. Furthermore, the CT Band Index may be manually compared to CT Band Related Index and a diagnosis and/or treatment may be manually determined based upon the CT Band Related data. CT Band Related data may also be manually updated and the CT Band Index generated may be manually stored and/or outputted.

Figure 7:
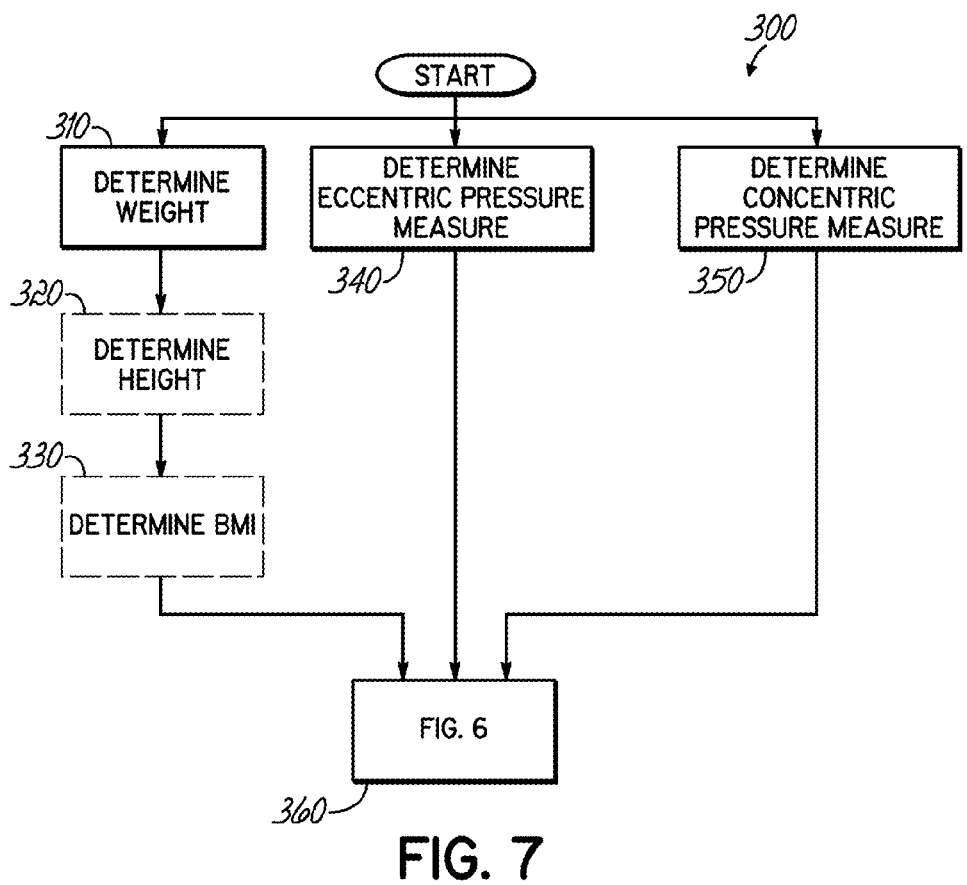
FIG. 7 is a flowchart of a determining an eccentric, a concentric and a weight based value routine executed in an environment of FIGS. 1 and 2.

Turning now to routine 300 in FIG. 7, routine 300 illustrates a determining an eccentric, a concentric and a weight based value routine consistent with the principles of the present invention. Routine 300 may be used to determine the inputs that are received in connection with block 210 of FIG. 6. At least one eccentric pressure value, at least one concentric pressure value, and at least one weight based value may be determined by routine 300, either manually or automatically.

Turning to routine 300, the weight of a patient may be determined in block 310. For instance, the individual may stand on a sensor such as a scale. In some embodiments, the sensor may be attached to a computer, a handheld apparatus etc., and as such, the measurement may be automatically determined and this weight measurement may be used as the weight based value to generate the CT Band Index. The sensor may be attached to a computer, hand held apparatus etc., by a wire or may interface wirelessly. As an example, the weight reading may be automatically determined by the sensor and transmitted to a computer. Conventional techniques for transmitting and/or receiving data by wires and wirelessly may be used to accomplish this. Additionally, the weight of an individual may also be determined manually by a user (e.g., clinician, physical therapist, nurse, etc.) by having the individual stand on a sensor such as a scale and the user may manually read the weight from the scale.

Next, the height of the patient may be determined and may be used to determine the patient's BMI. The height may also be determined automatically or manually utilizing a sensor. Next, if a height is determined then the BMI may be determined in block 330. The BMI may be automatically generated by using the BMI formula and weight and height measurements. The BMI may also be determined manually. If the BMI is determined, this BMI value may be sent as an input to routine 200 in FIG. 6 (i.e., block 360) or alternatively if a BMI is not calculated, then the determined weight may be sent as an input to routine 200 in FIG. 6 (i.e., block 360). The determined BMI or the weight may thus serve as the weight based value input of routine 200.

Those of ordinary skill in the art may also appreciate that multiple weight values and/or BMI's may be determined and an average of a multitude of these may be used as input. Moreover, a weight based value consistent with the present invention could be practically any measurement that includes a weight measurement.

Next, block 340 determines an eccentric pressure value. An eccentric pressure value may be created by having an individual stand on an inclined platform. The incline on the platform may be less than about one hundred and eighty degrees, preferably less than about ninety degrees from the horizontal surface. However, the angle may be less than about eighty-five degrees, less than about eighty degrees, less than about seventy-five degrees, less than about seventy degrees, less than about sixty-five degrees, less than about sixty degrees, less than about fifty-five degrees, less than about fifty degrees, less than about forty-five degrees, less than about forty degrees, less than about thirty-five degrees, less than about thirty degrees, less than about twenty-five degrees, less than about twenty degrees, less than about fifteen degrees, less than about ten degrees, and/or less than about five degrees. The incline on the platform may be more preferably less than about fifty degrees from the horizontal surface. Preferably, the incline platform is angled from about thirty-five degrees to about fifty degrees from the horizontal surface. Preferably, the angle is from about ten degrees to about sixty degrees.

More preferably, the inclined platform is angled from about thirty five degrees to about forty five degrees from the horizontal surface. Even more preferably, the incline platform is angled about thirty five degrees from the horizontal surface or the inclined platform is angled about forty five degrees from the horizontal surface. A platform may be designed with the feet in the normal base of gait with each foot abducted from the midline of the body by about fifteen degrees. The medial margin of each heel may be about two inches from the midline of the platform. Also, the platform may be designed with heel cradles and an open forefoot to accommodate all sizes of feet. The inventor has designed a platform generally with these characteristics.

A sensor, for example, resembling a dot, may also be placed on the bottom of the forefoot for determining an eccentric pressure value. The sensor may be placed beneath about the second metatarsal head, approximately about the second toe. The placement of the sensor may be determined by marking the base of the toe with a felt tipped pen at the most proximal aspect of the 1st and 2nd interspaces. The toe may be straightened and the length of the toe may then be measured from the mark distally to the tip of the toe. The measured length of the toe may then be used to establish a second mark an equidistance proximal to the mark. The second mark may represent the plantar aspect of the second metatarsal head.

The sensor may from about less than ten centimeters, preferably the sensor may be from about less than five centimeters. More preferably, the sensor may be from about two centimeters to about four centimeters and even more preferably, the sensor may be from about two and a half centimeters to about three centimeters. Most preferably, the sensor is about two centimeters. In particular, the sensor size may affect the duplication of the measurement, as such, those of ordinary skill in the art may appreciate that the size of the sensor may be selected based upon the ease of duplicating measurements.

The sensor may also be composed of multiple sensors, for example, a sensor that is about two centimeters may be composed of two one centimeter sensors. Additionally, a one centimeter sensor may be placed under each metatarsal head in some embodiments. The sensor may be a pressure sensor such as those designed by Sensor Products, LLC, located in East Hanover, N.J. As such, an eccentric contraction of the CT Band in the normal base of gait may be determined by the sensor. Additionally, a second sensor such as the first sensor may be placed about the bottom of the heel. The secondary sensor may be used to define sway during eccentric contraction measurements. The location of the secondary sensor may be the center of the plantar heel. This location may be determined by bisecting the plantar heel from medial to lateral. A second measurement may be made from the posterior heel to the center of the heel. A central mark established on the plantar heel that may be equidistant from the medial lateral and posterior aspects of the plantar heel. The second sensor may be placed on the plantar heel at a position equidistant from medial, lateral and posterior heel. Generally, this second sensor may be used to determine the center of gravity and as such may be utilized to remove sway from the measurement. As such, the eccentric pressure value readings may be recorded when the center of gravity is midway between the forefoot sensor or the first sensor and the rear foot sensor or the second sensor.

Sway can also be inhibited by having an individual hold on to a rail, approximately waist high for stability. Additionally, eccentric pressure values should be determined expeditiously. Preferably, a reading of the eccentric contraction should be measured within about ten seconds of initiating the measurement as an eccentric contraction may lessen over time due to fatigue.

Patients may be barefoot or in socks during the measurements. However, the eccentric and/or concentric pressure values may be determined while a patient is wearing a shoe (e.g., a diabetic shoe, a cast, etc.). It is worth nothing though that wearing a shoe may affect the reading and may lead for example to a lower CT Band Index. Wearing a clog may affect the measurement and lead to a lower CT Band Index than the CT Band Index if the patient had not been wearing the clog. Nonetheless, it may also be helpful to determine a CT Band Index before wearing a shoe and once again while a patient is wearing the shoe to determine how a patient's CT Band Index changes, and whether the shoe may be used as part of the patient's treatment. Furthermore, other modification may be made in some embodiments (e.g., placement of the sensor, size of the sensors, etc.).

In some embodiments, the determination of the eccentric pressure value or at least one eccentric pressure value may be done automatically, for instance, the computer may engage a sensor by a wire or wirelessly and the eccentric pressure value may be determined automatically from the sensor. Moreover, the sensor may even be incorporated into an apparatus that determines automatically the eccentric pressure value, or a clinician may manually determine the eccentric pressure value. Nonetheless, the eccentric pressure value determined either manually or automatically or a combination of both may be sent to routine 200 in FIG. 6 (i.e., block 360) and used by routine 200 to generate a CT Band Index for the patient.

Next, block 350 determines the concentric pressure value and this pressure value may also be sent to routine 200 of FIG. 6 (i.e., block 360). To measure a concentric pressure value, a patient may be asked to jump vertically with both arms extended at their sides. The patient may be asked to jump as high as possible while keeping their arms at their sides. While jumping, the patient may also wear a sensor as described herein above to record the concentric contraction. Preferably, patient should jump more than once and multiple measurements should be recorded. For instance, the patient may be asked to jump three times and the three measurements should be recorded. The patient may be to preform test jumps prior to obtaining the measurements such as one or two test jumps.

Alternatively, the patient may be asked to walk instead of jump while wearing the sensors to determine a concentric pressure value. Similarly, a walking patient may also be able to produce a concentric contraction and this may be measured to obtain a concentric pressure value to generate the CT Band Index for the patient. Additionally, a walking patient may be able to produce a concentric contraction by running. Furthermore, a concentric pressure value may also be expressed as casual and explosive load. Casual load may be the maximal load applied to the center of pressure while walking and may be measured at three separate periods once normal gait has been established. Explosive load may occur with the patient jumping from a squatting position to a point as high as they can possibly jump with their arms extended at their sides. Explosive load may be the average of three jumps. In some instances, casual load (e.g., walking) may have more variables such as stride length, cadence, etc. that may make duplication more difficult in comparison to explosive load (e.g., jumping). As such, explosive load (e.g., jumping) may be used to normalize the data. Nonetheless, as indicated above, the concentric pressure value may be automatically determined, for example, when the sensor is connected to a computer by a wire or interfaces wirelessly with a computer, or may be calculated manually, for example, by a clinician reading the sensor, or by a combination of both.

Those of ordinary skill in the art will appreciate that a value that is indicative of muscle strength may also be generated for other lever arms or muscle or muscle groups in a patient that are not the CT Band. Moreover, this value may be indicative of non-reciprocal muscle strength and/or indirectly indicative of non-reciprocal muscle strength. Muscle strength testing may be conducted in some embodiments in connection with other lever arms such as a knee, an elbow, a jaw, a hip (e.g., flexors of the hip), to name a few. Furthermore, those of ordinary skill in the art may come up with additional areas for which to conduct muscle strength testing and/or additional applications for muscle strength testing consistent with the principles of the present invention. As such, muscle strength testing of the CT Band as well as other areas of the human body are within the scope of the present invention. Furthermore, muscle strength testing of entities other than humans, for example, mammals such as dogs, cats, etc. or other animals, reptiles, etc. may be within the scope of the present invention. Furthermore, as such, the techniques disclosed herein for generating a value indicative of muscle strength, including indicative of non-reciprocating muscle strength and/or indirectly indicative of non-reciprocating muscle strength, may be used to treat a patient, which may be a human or a non-human, for a condition(s) associated with a lever arm.

In particular, either manually, automatically, or by a combination of both: 1) an eccentric pressure value may be determined for a muscle or muscle group, 2) a concentric pressure value may be determined for the muscle or the muscle group, and 3) generating an muscle strength measurement of the muscle or muscle group. Furthermore, these two values may be added together to generate a non-reciprocal muscle strength measurement. As such, this may include the CT Band as well as another muscle or muscle group. The measurement may be non-reciprocal muscle strength measurement and/or indirect non-reciprocal muscle strength measurement and may include a weight based value.

For instance, one of ordinary skill in the art may determine that non-reciprocal muscle activity may be occurring at a location where there is negative muscle work. In particular, negative contraction can be sustained for a much longer period of time than can be positive contraction in the CT Band. From an evolutionary standpoint, it's all about work; how can one conserve energy by utilizing negative contraction over a sustained period. As such, negative muscle work and/or an increase usage of negative work may be found in the body where there is sustained work.

One example may be the flexors of the hip. During gait, the hip flexors may employ negative work to decrease the range of motion of the hip. This may enable the torsion from the upper body to be transferred into the leg and ultimately delivered to the CT Band via the biceps muscles of the thigh, crossing the knee (more negative work). This may be referred to as secondary load, for example, load that is transferred to the CT Band from a proximal source.

Continuing on with the hip flexor example, positive contraction may only come into play at the end of the gait cycle, lifting the leg off of the ground to begin another gait cycle. The hip flexors use negative muscle work and work as a lever arm. However, the positive contraction comes into play as a different function. As such, the lever arm of the hip may be using negative force as oppose to the CT Band that is a lever arm utilizing combined negative and positive force.

Figure 8:
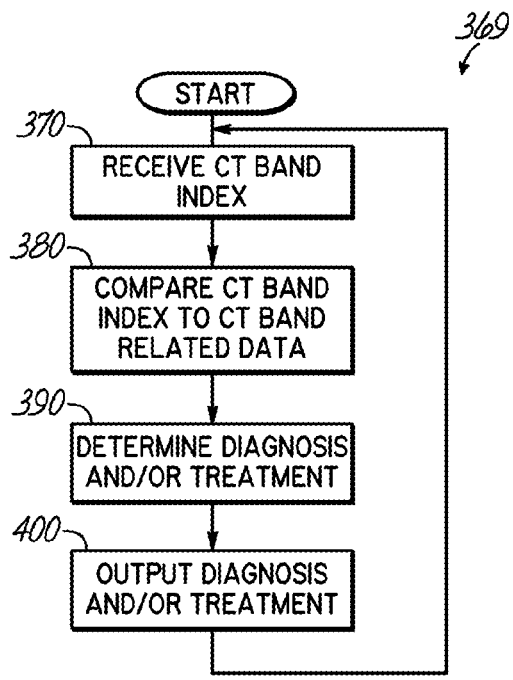
FIG. 8 is a flowchart of a comparing CT Band Index to CT Band related data routine executed in an environment of FIGS. 1 and 2.

Turning now to FIG. 8, which illustrates routine 369, routine 369 is an exemplary comparing CT Band Index to CT Band related data routine consistent with the principles of the present invention. In particular, routine 369 is similar to routine 200. One of the differences, however, is that an eccentric, concentric, and weight based value inputs are received in routine 200 and then the generated CT Band Index is comparing to CT Band related data, whereas in routine 369, the CT Band Index is received as an input and this CT Band Index is compared to CT Band related data. Specifically, in block 370, a CT Band Index, which may be generated manually by a clinician or automatically by routine 200 of FIG. 6 may be received, for example, via a web portal, and this CT Band Index may be compared with CT Band related data, for example, in a server in block 380. Similarly, a diagnosis and/or treatment may be determined in block 390 and output in block 400.

As an example, a clinician may have a handheld computer in his or her office that interfaces either by wires or wirelessly with sensors and the sensors are placed on a patient to measure the concentric and eccentric contractions as well as the weight and/or BMI. This hand held computer may be then be connected by the clinician to another computer via a USB port, for instance, or it may connect wirelessly and transmit the CT Band Index through a web portal. The CT Band Index may then be compared to CT Band data that is stored on the server with CT Band related data from the patients of clinicians from around the country or around the world. Next, after the comparison, a diagnosis and/or treatment may be displayed for the clinician on his or her computer screen and the clinician may determine whether or not he or she wants to proceed with the indicated diagnosis and/or treatment.

Those of ordinary skill in the art may appreciate that the CT Band Index may be used to determine those patients who are susceptible to CT Band Syndrome. The inability of the CT Band to sustain repetitive loading may result in injury to the CT Band and these injuries are generally referred to herein as CT Band Syndrome or conditions associated with a lever arm comprising from about a calf of the leg to about a forefoot of the leg.

Factors that may contribute to CT Band Syndrome may be physiological, mechanical or a combination of both. Physiological factors that may contribute to weakening of the CT Band may include increased age, weight gain and obesity, malnutrition, and/or poor physical condition. Mechanical reasons for increased stress to tissue structures of the CT band may include increased repetition of load, increased duration of load, increased amount of load, and/or eccentric loading. An example of conditions that are included in CT Band Syndrome in non-neurotrophic patients may include Achilles tendonitis (within the body of the tendon), Insertional Achilles tendonitis, Posterior tibial tendon dysfunction, Peroneal tendonitis, Retrocalcaneal bursitis, Sever's Disease, Plantar fasciitis, Plantar fibromatosis, Tarsitis (acute ankle/tarsal bone pain), Flat top talus, Tarsalgia (chronic ankle/tarsal bone pain), Cuboid syndrome, Lateral column syndrome, Metatarsal fractures of the lateral column of the foot, and Midfoot osteoarthritis (non-traumatic onset). CT Band Syndrome conditions in neurotrophic populations may include all of the above, Charcot joints, Predeliction for forefoot ulcerations.

In particular, changes in the CT Band Index can be monitored and may be suggestive of pathology or healing. Furthermore, the CT Band Index may be used for treating a patient. Treating a patient may include diagnosing and/or treatment, however, treating is used in a flexible manner herein and may include preventive treatment, no treatment, diagnosing, etc. Nonetheless, increases in a patient's CT Band Index may indicate the following: increase in static load (e.g., load that the lever arm is moving such as the weight of the patient and/or total duration and/or frequency of body weight), increase in concentric contraction, and/or increase in eccentric contraction. Decreases in a patient's CT Band Index may indicate the following: decrease in static load, decrease in concentric contraction, and/or decrease in eccentric contraction.

Clinical applications for the CT Band Index may include the following:

Medical/Surgical

Pre and post-op measurements of the efficacy of (1) gastrocnemius recession and (2) tendo Achilles lengthening procedures.
Determination of the contribution of load bearing on diabetic forefoot ulcerations.
Evaluation of lateral column syndrome, tarsitis and related load bearing tarsal bone pathomechanics.
Measurement of patients before and after treatment for plantar fasciitis, Achilles tendonitis, Sever's Disease and an ability to monitor change in these conditions.
Evaluation of eccentric or unstable midfoot CT Band syndrome conditions such as posterior tibial tendonitis (PTTD) and peroneal tendonitis.
Effectively gauge return to work for patients with CT Band Syndrome pathology.
Pedorthics/Shoes Evaluate the efficacy of anterior rocker soles.
Evaluate the efficacy of clogs and 'off loading' forefoot shoe designs.
Evaluate off loading for diabetic foot wear.
Sports Quantitatively define return to game parameters for CT Band Syndrome injuries.
Help parents understand treatment options for children with Sever's Disease.
Evaluate the impact of calf stretching on CT Band pathology in athletes.
Quantify treatment plans for athletes based upon changes in the CT Band Index.
Quantify exercise plans for athletes based upon CT Band injuries and changes in the CT Band Index.

CT Band Syndrome may be treated as follows. As a lever arm, which are generally uniplanar, the CT Band may be most effective when load is carried in a single body plane. The majority of work performed by the CT Band may occur within the sagital plane. In many cases, CT Band Syndrome may be the result of excessive or prolonged load applied in the sagital plane. Treatment of CT Band Syndrome secondary to sagital plane load biomechanics may be accomplished by the following:

Shoe Modification

Heel lifts
Wedge sole shoes
Forefoot and rearfoot rocker shoe modifications
Physical Therapy Calf stretching
Surgery Gastocnemius recession
Tendo-Achilles lengthening Moreover, CT Band Syndrome may also result from the deviation of normal load bearing in the sagital plane. Deviation from sagital plane to the frontal or transverse planes may decrease the efficacy with which the CT Band carries load. As a result, deviation from the sagital plane may result in ineffective locomotion and an increase in applied stress to each of the three segments of the CT Band. There are a number of common foot conditions that may contribute to the deviation of CT Band away from the sagital plane. These conditions may include but are not limited to congential deformities such as metatarsus adductus, talipes equino varus (clubfoot) or acquired deformities such as posterior tibial tendon dysfunction. Each condition results in a deviation of normal load bearing in the sagital plane. The result is an increase in applied stress and possible tissue failure (strain). If stain cannot be repaired by the body in a reasonable time period, the overuse syndrome (CT Band Syndrome) is initiated.

Treatment of CT Band Syndrome secondary to transverse plane or frontal plane deformities may include realignment of the deformity in an attempt to recreate optimal delivery of sagital plan load. Methods used to treat CT Band Syndrome secondary to transverse plane pathology may include:

Shoe Modifications

Rigid shank
Stiff leather sole shoes
Leather Oxfords Thomas heels/reverse Thomas heels
Foot/Ankle Bracing Rigid AFO/SMO
Dynamic AFO/SMO
Arizona Brace
Foot orthotic
Surgery Metatarsus adductus correction
Medial or lateral column shortening or lengthening
Flatfoot reconstruction
Triple arthrodesis with or without wedging
Calcaneal displacement osteotomy
Subtalar arthroeresis The pathomechanics of the CT Band have traditionally been studied as isolated problems. However, by defining the CT Band an inter-relationship of these conditions and utilizing the CT Band Index, diagnosis and/or treatment of patients may be improved.

On a different note, as discussed above, attempts to directly test the lever arm (i.e., the leg, ankle and foot) may prove difficult to duplicate in a clinical setting for a variety of reasons. Those reasons include the inability to define many of the physical properties of the lever; length of the effort arm (tibia), length of the resistance arm (foot), and location of the fulcrum (ankle which is always moving). Indeed, the physical properties of a lever may be easy to measure when defining basic levers like a seesaw or a nut cracker, but physical properties become fluid and dynamic in the human model creating a number of variables. The variables may make direct measurement very difficult.

Hence, the discussion hereinabove focused on a way to use an indirect method of measurement by isolating and measuring the individual forces generated within the CT band. These are the forces referred to as eccentric and concentric contractions, with two separate tests measuring the eccentric and concentric force. These tests involved having a subject (a) stand on an incline block while forefoot pressures were measured (eccentric) and (b) measuring the peak force generated with a vertical jump (concentric). Instead, of the incline block, a boot ("the boot") like device may be utilized. The boot may be a surgical shoe made rigid by a ¼" thick insert of polypropylene or about a ¼" thick insert of polypropylene. An articulated metal stirrup brace that would enable attachment of the shoe to the leg of a patient and gain greater control over ankle range of motion may also be part of the boot. The ankle hinge of the stirrup brace may be preset to about 15 degrees of both dorsiflexion and plantarflexion (about 30 degrees total range of motion). A series of four rows of capacitance sensors, such as those from Sensor Products, Madison N.J., may be placed on the sole of the shoe. This range of sensors may be aligned to capture peak pressure readings from shoe sizes of women's about 5 to a men's size about 11. Readings may be taken of peak pressure with dorsiflexion (eccentric) and plantarflexion (concentric). And again, this approach focuses on isolating and recording peak eccentric and peak concentric values.

However, the inter-examiner and intra-examiner reliability of testing with the boot may be low. To improve reliability, existing testing methods like the F-scan or emed (discussed further below) may instead be utilized to determine the CT band index. Indeed, the products made by companies like Novel and Tekscan may generate more accurate and reliable test outcomes. As such, the eccentric and concentric pressures may be measured with the same single test that measures peak forefoot pressure. When measured during gait, peak forefoot pressure may represent the combined forces previously isolated and measured as eccentric and concentric. Peak forefoot pressure is generally a measurement that is part of existing flat mat and in-shoe pressure testing devices. Thus, the CT Band Index may be determined with a combined eccentric and concentric value instead of an individual eccentric value and an individual concentric value.

As such, instead of defining the CT Band Index as follows:

(Eccentric value+Concentric value)×BMI=CT Band Index

The peak forefoot measurement during gait may be the combine value of eccentric and concentric values. Therefore, the CT Band Index may be defined as follows:

Peak forefoot pressure value×BMI=CT Band Index

Alternatively, the CT Band Index may be defined as follows:

a combination value×BMI=CT Band Index

The combination value is representative of both eccentric and concentric pressure values. The combination value may be the peak forefoot pressure value. Moreover, in both instances, BMI may be replaced with some other weight based value consistent with the principles of the present invention.

Novel manufactures several different types of pedal pressure measurement devices. The first line is called emed. Emed includes three different flat mat systems. The second Novel system is a mobile system called pedar. The basis of the Novel system is capacitive sensor technology. Each of the Novel devices (flat mat and in-shoe) may be used to determine the CT Band Index. Tekscan offers several different flat mat systems and a mobile in-shoe system called F-Scan. Tekscan also employs capacitive sensor technology. Each of the Tekscan devices (flat mat and in-shoe) may be used to determine the CT Band Index.

In particular, testing for the CT Band Index, using the Novel and Tekscan devices, may be performed in the ambulatory patient as follows. First, the gait may be fairly well controlled when the cadence of gait is regulated. For instance, a metronome may be utilized to define "x" number of steps/minute. By testing in this manner, the gait may be regulated and result in a more reliable data set. The determined CT Band Index may then be utilized to impact the course of clinical care as described hereinabove. Thus, the Novel and Tekscan devices may be utilized to determine the CT Bank Index, an indirect measurement of the lever aim, and advantageously may be 1) affordable, 2) easily used in a clinical setting, 3) provide data that is accurate and pertinent to clinical care, and/or 4) produce data that is reliable when performed by multiple providers. Indeed, the CT Band Index may represents the first quantitative aspect of pressure sensing that Novel and Tekscan would have to offer to clinicians. As such, this quantitative data may enable the Novel and Tekscan devices to define injuries, monitor the progress of treatment, and compare patient data as normalized data (i.e., multiple patients with the same condition comparing CT Band Index values) as generally described hereinabove. Indeed, the CT Band Index may add new clinical value and significant commercial value to these products.

Various modifications may be made to the illustrated embodiments without departing from the spirit and scope of the invention. Therefore, the invention lies in the claims hereinafter appended.

What is claimed is:

1. A method of treating a patient for a condition associated with a lever arm, the method comprising:
   (a) placing a first sensor against the patient's lever arm;
   (b) measuring with the first sensor a pressure value associated with the lever arm of the patient at a determined location on the lever arm;
   (c) placing a second sensor against the patient;
   (d) determining with the second sensor at least one weight based value of the patient; and
   (e) receiving data from the first and second sensors into a computing device, the computing a value that is indicative of muscle strength of the lever arm using the determined values.

2. The method of claim 1, further comprising comparing the computed value to at least a portion of lever arm related data comprising at least one previously computed value.

3. A computer implemented method of treating a patient for a condition associated with a lever arm comprising a leg, ankle, and foot, the computer implemented method comprising:
   (a) placing a sensor against the patient's lever arm;
   (b) measuring with the sensor a pressure that is indicative of muscle strength of the lever arm at a determined location on the lever arm;
   (c) receiving data from the sensor into a computer, the computer comparing the measured pressure to at least a portion of lever arm related data comprising at least one previously generated value; and
   (d) outputting a result from the comparison from the computer.

4. The computer implemented method of claim 3, further comprising determining at least one of diagnosis or treatment based upon the comparison.

5. The computer implemented method of claim 3, further comprising automatically multiplying a peak forefoot pressure value and a weight based value, wherein the peak forefoot pressure value is a combination of an eccentric pressure value and a concentric pressure value.

6. The computer implemented method of claim 3, further comprising automatically generating the value by multiplying a combination value and a weight based value, wherein the combination value is a combination of an eccentric pressure value and a concentric pressure value.

7. A computer implemented method of treating a patient for a condition associated with a lever arm comprising a leg, ankle, and foot, the computer implemented method comprising:

(a) placing first and second sensors against the patient's lever arm;
(b) measuring with the first sensor at least one eccentric pressure value associated with the lever arm of the patient at a determined location on the lever arm;
(c) measuring with the second sensor at least one concentric pressure value associated with the lever arm of the patient at a determined location on the lever arm;
(d) receiving data from the first and second sensors, and at least one weight based value of the patient, into a computing device; and
(e) the computing device generating a value that is indicative of muscle strength of the lever arm using the determined values.

8. The computer implemented method of claim 7, further comprising repeatedly measuring at least one of the eccentric pressure value, the concentric pressure value, or the weight based value during a course of treatment.

9. The computer implemented method of claim 8, wherein measuring comprises utilizing at least one sensor.

10. The computer implemented method of claim 7, wherein generating comprises automatically generating the value by summing the concentric pressure value and the eccentric pressure value and multiplying the sum by the weight based value.

11. The computer implemented method of claim 7, further comprising outputting the generated value.

12. The computer implemented method of claim 7, further comprising collecting lever arm related data comprising at least one previously generated value.

13. The computer implemented method of claim 7, further comprising comparing the generated value to at least a portion of lever arm related data comprising at least one previously generated value.

14. The computer implemented method of claim 13, further comprising determining at least one of diagnosis or treatment based upon the comparison.

15. An apparatus, comprising:
(a) computer readable medium; and
(b) program code resident in the computer readable medium and configured to treat a patient for a condition associated with a lever arm comprising a leg, ankle, and foot, the program code configured to receive at least one pressure value associated with the lever arm of the patient, receive at least one weight based value of the patient, and generate a value that is indicative of muscle strength of the lever arm using the determined values.

16. The apparatus of claim 15, further comprising at least one sensor.

17. The apparatus of claim 16, wherein the sensor is associated with a flat mat device.

18. The apparatus of claim 16, wherein the sensor is associated with an in-shoe device.

19. The apparatus of claim 15, wherein the program code is further configured to determine at least one of the eccentric pressure value, the concentric pressure value, or the weight based value.

20. The apparatus of claim 19, wherein the program code is further configured to utilize at least one sensor.

21. The apparatus of claim 15, wherein the program code is further configured to automatically generate the value by summing a concentric pressure value and an eccentric pressure value and multiplying the sum by the weight based value.

22. The apparatus of claim 15, wherein the program code is further configured to output the generated value.

23. The apparatus of claim 15, wherein the program code is further configured to collect lever arm related data comprising at least one previously generated value.

24. The apparatus of claim 15, wherein the program code is further configured to compare the generated value to at least a portion of lever arm related data comprising at least one previously generated value.

25. The apparatus of claim 24, wherein the program code is further configured to determine at least one of diagnosis or treatment based upon the comparison.

26. The apparatus of claim 15, further comprising at least one processor coupled to the computer readable medium and configured to execute the program code.

27. The apparatus of claim 15, wherein the computer readable medium is a removable medium configured to be installed in a computer for execution of the program code in the computer.

28. The apparatus of claim 15, wherein the program code is further configured to collect lever arm related data comprising at least one previously generated value for a different patient.

29. The apparatus of claim 15, wherein the program code is further configured to compare the generated value to at least a portion of lever arm related data comprising at least one previously generated value for a different patient.

30. The apparatus of claim 15, wherein the program code is further configured to automatically generate the value by multiplying a peak forefoot pressure value and the weight based value, wherein the peak forefoot pressure value is a combination of an eccentric pressure value and a concentric pressure value.

31. The apparatus of claim 15, wherein the program code is further configured to automatically generate the value by multiplying a combination value and the weight based value, wherein the combination value is a combination of an eccentric pressure value and a concentric pressure value.

32. A method of teaching a user how to treat a patient for a condition associated with a lever arm comprising a leg, ankle, and foot, using a computing device, the method comprising:
(a) generating a display on the computing device prompting the user to determine a pressure value associated with the lever arm of the patient;
(b) generating a display on the computing device prompting the user to determine at least one weight based value of the patient;
(c) generating a display on the computing device prompting the user to generate a value that is indicative of muscle strength of the lever arm using the determined values; and
(d) generating a display on the computing device prompting the user to interpret the generated value.

33. The method of claim 32, further comprising prompting the user to multiply a peak forefoot pressure value and the weight based value, wherein the peak forefoot pressure value is a combination of the eccentric pressure value and concentric pressure value.

34. The method of claim 32, further comprising prompting the user to multiply a combination value and the weight based value, wherein the combination value is a combination of an eccentric pressure value and a concentric pressure value.

* * * * *